(12) United States Patent
Subramanyam et al.

(10) Patent No.: US 8,071,077 B2
(45) Date of Patent: Dec. 6, 2011

(54) ORAL COMPOSITIONS CONTAINING BIPHENOL ANTIBACTERIAL COMPOUNDS

(75) Inventors: Ravi Subramanyam, Belle Mead, NJ (US); Prem Sreenivasan, Westfield, NJ (US)

(73) Assignee: Colgate-Palmolive Company, New York, NY (US)

( * ) Notice: Subject to any disclaimer, the term of this patent is extended or adjusted under 35 U.S.C. 154(b) by 953 days.

(21) Appl. No.: 11/287,930

(22) Filed: Nov. 28, 2005

(65) Prior Publication Data

US 2006/0140880 A1  Jun. 29, 2006

Related U.S. Application Data

(60) Provisional application No. 60/640,160, filed on Dec. 29, 2004.

(51) Int. Cl.
*A61K 8/00* (2006.01)
*A61Q 11/00* (2006.01)

(52) U.S. Cl. ................. 424/49; 424/52; 424/57; 424/58

(58) Field of Classification Search .................... 424/49, 424/52, 57, 58
See application file for complete search history.

(56) References Cited

U.S. PATENT DOCUMENTS

| | | | |
|---|---|---|---|
| 3,429,963 A | | 2/1969 | Shedlovsky |
| 5,292,526 A | | 3/1994 | Gaffar et al. |
| 5,356,615 A | * | 10/1994 | Gaffar .............................. 424/49 |
| 5,472,684 A | | 12/1995 | Nabi et al. |
| 6,379,652 B1 | | 4/2002 | Liu et al. |
| 2003/0049303 A1 | * | 3/2003 | Ning et al. ..................... 424/439 |
| 2006/0140880 A1 | | 6/2006 | Subramanyam et al. |

FOREIGN PATENT DOCUMENTS

| | | |
|---|---|---|
| JP | 07033649 | 2/1995 |
| JP | 09176074 | 7/1997 |
| JP | 9278638 | 10/1997 |
| JP | 2004292392 | 10/2004 |
| WO | WO 97/10800 | 3/1997 |
| WO | WO 01/82922 | 11/2001 |
| WO | WO 01/85116 | 11/2001 |

OTHER PUBLICATIONS

Fujisawa, S. et al. "Application of *bis*-eugenol to a zinc oxide eugenol cement". Journal of Dentistry 27. (1999). pp. 291-295.
Kobayashi, Akio et al., "Eugenol and isoeugenol dimmers as bactericides, fungicides, and inflammation inhibitors", Chemical Abstracts Services (1997) JP 09176074 Accession No. 1997:580683.
Murakami et al. (Biochemical Pharmacology 66 (2003) 1061-1066).
Mergenhagen et al.( J Dent Res 1970 49: 256-261).
Silverman, Richard B. ("The Organic Chemistry of Drug Design and Drug Action". London: Academic Press Ltd., 1992.).
Delogu et al."Enantiopure 2,2- dihidroxi 3,3'- dimethoxy-5- ,5' diallyl-6, 6'-dibromo-1, 1'-biphenyl: a conformationally stable $C_2$ - dimer of a eugenol derivative", Tetrahedron: Asymmetry (2004) 15, 275-282.
Baehni, et al. "Anti-plaque agents in the prevention . . . " Oral Diseases (2003) 9, 23-29.
Marsh, "Plaque as a biofilm . . . "Oral Diseases (2003) 9,16-22.
Botelho, "Fractional Inhibitory Concentration . . . "J. of Densistry 28 (2000) 565-570.
Furiga et al. "In Vitro anti-bacterial and anti-adherence" J. Applied Microbiology 2008, 105:1470-1476.
J.M. ten Cate et al. "Procedures for Establishing Efficacy . . . " J. Dent. Res. 73 (3): 695-703, Mar. 1994.

* cited by examiner

*Primary Examiner* — Patricia A Duffy
*Assistant Examiner* — Chris E Simmons
(74) *Attorney, Agent, or Firm* — Nikhil A. Heble

(57) ABSTRACT

Antiplaque oral compositions are provided that contain an orally acceptable carrier and an antibacterial effective amount of the compound of formula (I). In various embodiments, the compositions contain from about 0.001% to about 10% by weight of the compound of formula (I).

18 Claims, No Drawings

ORAL COMPOSITIONS CONTAINING BIPHENOL ANTIBACTERIAL COMPOUNDS

CROSS REFERENCE TO RELATED APPLICATIONS

This application claims priority to U.S. Provisional Patent Application Ser. No. 60/640,160, filed Dec. 29, 2004, the contents of which are incorporated herein by reference.

BACKGROUND OF THE INVENTION

A number of disease conditions are associated with the action of bacteria in the oral cavity. For example, gingivitis, an inflammation or infection of the gums and alveolar bones, is generally believed to be caused by plaque causing bacterial and the toxins formed as by-products from the bacteria. In addition, plaque provides a locus for calculus or tartar formation. Periodontitis is generally believed to occur where unremoved plaque hardens into calculus (tartar), which affects the periodontal ligaments. As plaque and tartar continue to build up, the gums begin to recede, which can lead to continued inflammation, infection and potentially the loss of teeth.

To prevent or treat these diseased conditions, antibacterial agents may be incorporated into oral care compositions such as toothpaste and mouthwashes or rinses. Application of antibacterial compositions in the oral cavity tends to retard plaque formation and related oral infections. It is also common to provide oral compositions containing components that remove or prevent the build-up of tartar. Effective antitartar agents, such as phosphates, are believed to work in-part by interfering with crystalline growth of hydroxyapatite on the tooth surface.

The antiplaque efficacy of antibacterial compounds in a dentifrice composition depends on a number of factors, including the presence of other ingredients that may interfere with its action. For example, certain cationic antibacterial compounds and certain nonionic antibacterial compounds lose their effectiveness when formulated with certain anionic surfactants or other anionic active ingredients, such as tartar control phosphates. In many instances, it is preferred to use antibacterial compounds that do not show the adverse interactions with such anionic components.

Extracts from *Magnolia officinalis* (hereinafter "magnolia"), and especially from the bark, contain biphenol antibacterial compounds. The extracts have been found to have antibacterial effectiveness when formulated into, for example, toothpaste formulations.

Extracts prepared from natural sources such as magnolia are variable in composition and may contain many compounds other than the particular actives for which the extract is prepared. In addition, the composition of the extracts can vary from season to season and between different geographical regions. For these many reasons, it may be desirable to synthesize naturally occurring products such as those found in magnolia extracts.

BRIEF SUMMARY OF THE INVENTION

The invention is based in part on the discovery that a particular analog of magnolol—5,5'-dibutyl-2,2'-dihydroxy-1,1'-biphenyl—is effective as an antiplaque and antibacterial component of dentifrices and other oral compositions. The invention relates to various oral compositions containing the compound and an orally acceptable carrier. In various embodiments, antibacterial and antiplaque oral compositions are provided in the form of a paste or gel, a powder, a mouthwash or mouth rinse, a lozenge, chewing gum, an edible strip, and the like. The antibacterial compound is synthesized by Friedel-Crafts type acylation of a biphenol compound, followed by reduction to the end product.

DETAILED DESCRIPTION OF THE INVENTION

The invention provides a new antibacterial compound 5,5'-dibutyl-2,2'-dihydroxy-1,1'-biphenyl represented by the structure of formula (I), given below:

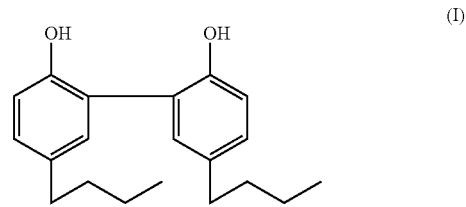

(I)

wherein any/all of the carbon atoms may be independently substituted or unsubstituted.

Antiplaque oral compositions are provided that contain an orally acceptable carrier and an antibacterial effective amount of the compound of formula (I) are also included. In various embodiments, the compositions contain from about 0.001% to about 10% by weight of the compound of formula (I). Without limitation, the orally acceptable carrier is a liquid carrier; a powder carrier; or a carrier that dissolves upon contact with saliva and other components of an oral environment, such as, for example a film. In other embodiments, the carrier can comprise a gum base. The oral compositions are provided variously in the form of a paste or gel, a powder, a mouth rinse, a lozenge, chewing gum, and an edible strip. Other forms of the composition include without limitation a liquid suitable for painting a dental surface, a wafer, a wipe or towelette, an implant, a dental floss, and forms that are edible or chewable by a small domestic animal such as a cat.

In other embodiments, the invention provides paste or gel compositions that contain at least one humectant, at least one abrasive material, and an antibacterial effective amount of the compound of formula (I). The paste or gel compositions may further comprise an anticalculus agent such as a phosphate compound, alternatively combined with synthetic anionic polycarboxylates. In an exemplary embodiment, the paste or gel composition comprises, for example:

0.001-5% by weight of compound of formula (I);
1-70% by weight humectant;
1-70% by weight abrasive compounds;
0.5-2.5% by weight tetrasodium pyrophosphate (TSPP); and
1-10% by weight sodium tripolyphosphate (STPP).

In other embodiments, the invention provides a method for inhibiting bacterial growth in the oral cavity of a subject animal, comprising applying to the oral surfaces of the subject animal an antibacterial composition comprising the compound of formula (I). In various embodiments, the method involves brushing the teeth, rinsing and/or applying to the oral surfaces compositions containing the compound of formula (I). As above, the method can be practiced by applying the antibacterial composition in a wide variety of forms such as pastes, gels, powder, mouth rinse, paint on gels, dissolvable or edible strips or films, chewing gum, lozenges, and the like.

In various embodiments, treatment of oral surfaces with antibacterial compositions containing the compound of formula (I) leads to reduction or elimination of plaque, to prevention or treatment of gingivitis, to amelioration of oral malodor, and prevention of periodontal disease. The MIC$_{50}$ of the compound of formula (I) has been found to be lower against certain oral bacteria than an analogous compound containing propyl groups.

The methods of preparing the compound of formula (I) include a step of reacting 2,2'-dihydroxy-1,1'-biphenyl with a butanoyl halide, such as butanoyl chloride, in the presence of a Lewis acid to form a carbonyl functional intermediate. Thereafter, the carbonyl functional intermediate is reduced to obtain the compound of formula (I).

Synthesis of the compound of formula (I) may be illustrated by the following scheme:

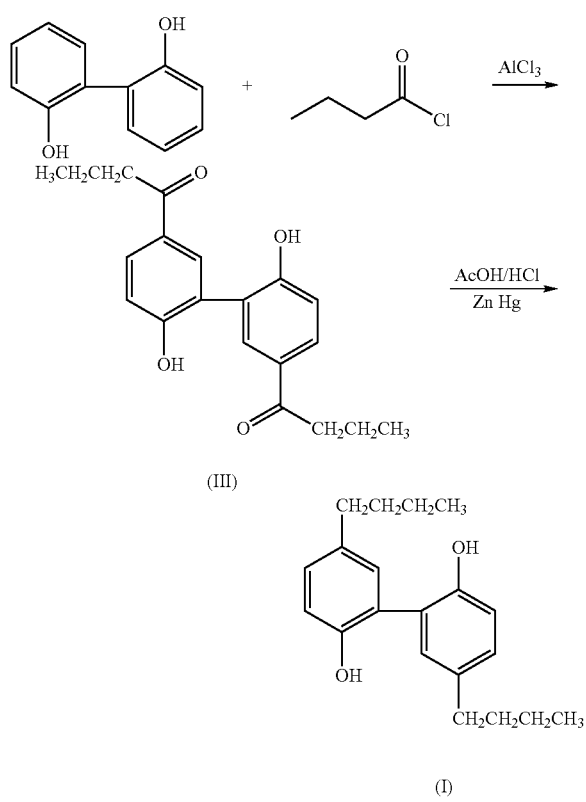

In a first step, a 2,2'-dihydroxy-1,1'-biphenyl is reacted with an alkanoyl halide (illustrated as, e.g., butanoyl chloride) containing four carbons in the presence of a Lewis acid (illustrated as, e.g., aluminum chloride). The reaction product is a carbonyl functional intermediate (III). The carbonyl functional intermediate is next reduced with conventional reducing agents to yield the final product (I). As shown in the scheme, reduction is accomplished by refluxing in acetic acid and HCl in the presence of a zinc mercury amalgam as a reducing agent (Clemmensen reduction). Other Lewis acids can be used in the first step, and other reducing agents can be used in the second step. Lewis acid catalysts and reducing agents and the conditions under which they can be utilized are well known in the art, and any such compounds and/or conditions may be used. Non-limiting reduction reactions include the Wolff-Kishner reduction, the Huang-Minlon modification, and reduction with lithium aluminum hydride/aluminum chloride.

The antibacterial compound of formula (I) is formulated with an orally acceptable carrier to provide oral compositions having a variety of forms.

The compositions of the invention contain an orally acceptable carrier and an antibacterial effective amount of the compound of formula (I). The carrier embraces all of the components of the oral composition except for the antibacterial compound of formula (I). The carrier may include components such as inactive ingredients, carriers, vehicles, and other active ingredients.

To illustrate in a non-limiting example for the case of pastes, the carrier can be a water/humectant system. Alternatively, the carrier component of a paste composition may be water, humectant, and other functional components other than the compound of formula (I). Whatever the context, a person of skill in the art recognizes that the paste composition contains both antibacterial compounds of the formula (I) and an orally acceptable carrier for the compound.

In a mouth rinse, the carrier may be, for example, a water/alcohol liquid component in which the antibacterial compounds of the formula (I) are dissolved, dispersed, suspended or otherwise incorporated. In a dissolvable lozenge, the carrier may be the solid matrix material that dissolves in the mouth to the oral surfaces in the mouth. In chewing gums, the carrier may be a gum base, while in an edible strip, the carrier may be one or more film forming polymers.

In all of the above examples, the oral composition, in whatever form, includes antibacterial compounds of the formula (I), a suitable carrier in an appropriate form, and other actives or functional materials needed to provide the oral compositions with desired properties.

In addition to the carrier, oral compositions of the invention contain an antibacterial effective amount of the compound of formula (I). The antibacterial effective amount may be preferred to be about 0.001% to about 10%, based on the total weight of the oral composition, for example about 0.01% to about 5% or about 0.1% to about 2%. The effective amount may vary depending on the form of the oral composition. For example, in pastes, gels, and powders, an effective amount may be at least about 0.01% and more preferably at least about 0.05%. Preferably, the compound of the formula (I) is formulated at 5% or less, preferably about 2% or less, and more preferably about 1% or less.

In mouth washes and rinses, the compound of the formula (I) may be about 0.001% (or 10 ppm) up to about 1%. Preferably, the compound represented by formula (I) may be present at about 0.5% or less or about 0.2%. Preferably, it is about 0.01% (100 ppm) or greater. In various embodiments, compound represented by formula (I) is present at about 0.03 to about 0.12% by weight.

In addition to the antibacterial compound of the formula (I), a number of active ingredients and functional materials are included in various compositions of the invention. Such materials include, without limitation, abrasives, humectants, surfactants, anticalculus agents, thickeners, viscosity modifiers, anticaries agents, flavorants, colorants, additional antibacterial agents, antioxidants, anti-inflammation components, and so on. Such components may be added to the pastes, rinses, gums, lozenges, strips, and other forms of the oral compositions of the invention according to known methods.

In various embodiments of the present invention, where the carrier of the oral care composition is solid or a paste, the oral composition preferably comprises a dentally acceptable abrasive material which may serve to either polish the tooth enamel, provide a whitening effect, or remove accumulated plaque. Non-limiting examples include silica abrasives such as silica gels and precipitated silicas. Commercial silicas may be used, such as ZEODENT® 115, marketed by J. M. Huber and SYLODENT® XWA, SYLODENT® 783 or SYLO- DENT® 650 XWA of the Davison Chemical Division of W. R. Grace & Co., Princeton, N.J. Other suitable dentifrice abrasives include, without limitation, sodium metaphosphate, potassium metaphosphate, tricalcium phosphate, dihydrated dicalcium phosphate, aluminum silicate, calcined alumina, bentonite or other siliceous materials, or combinations thereof.

The abrasive may be present in any amount, depending on the desired end result. In embodiments where the oral composition is in a solid or paste form, the abrasive material is generally present at about 10% to about 99% of the oral composition. In certain embodiments, the polishing material is present in amounts of about 10% to about 75% (for example, about 10% to about 40% or about 15% to about 30%) and from about 70% to about 99%.

In a still further embodiment, a composition of the invention comprises at least one humectant. Any orally acceptable humectant can be used, including without limitation polyhydric alcohols such as glycerin, sorbitol, xylitol and low molecular weight PEGs. One or more humectants may be present in a total amount of about 1% to about 70%, for example about 1% to about 50%, about 2% to about 25%, or about 5% to about 15% by weight of the composition.

The composition of the invention may include at least one surfactant useful, for example, to compatibilize other components of the composition and thereby provide enhanced stability, to help in cleaning the dental surface through detergency, and to provide foam upon agitation, e.g., during brushing with a dentifrice composition of the invention. Any orally acceptable surfactant, can be used. Suitable surfactants include without limitation water-soluble salts of $C_{8-20}$ alkyl sulfates, sulfonated monoglycerides of $C_{8-20}$ fatty acids, sarcosinates, taurates and the like. Illustrative examples of these and other classes include sodium lauryl sulfate, sodium coconut monoglyceride sulfonate, sodium lauryl sarcosinate, sodium lauryl isethionate, sodium laureth carboxylate and sodium dodecyl benzenesulfonate. Others include without limitation poloxamers, polyoxyethylene sorbitan esters, fatty alcohol ethoxylates, alkylphenol ethoxylates, tertiary amine oxides, tertiary phosphine oxides, dialkyl sulfoxides and the like. Further examples include without limitation derivatives of $C_{8-20}$ aliphatic secondary and tertiary amines having an anionic group such as carboxylate, sulfate, sulfonate, phosphate or phosphonate, such as cocoamidopropyl betaine. One or more surfactants may be present in a total amount of about 0.01% to about 10%, for example about 0.05% to about 5% or about 0.1% to about 2% by weight of the composition.

The composition may include an orally acceptable anticalculus agent. One or more such agents can be present. Suitable anticalculus agents include without limitation phosphates and polyphosphates (for example pyrophosphates), polyaminopropanesulfonic acid (AMPS), zinc citrate trihydrate, polypeptides such as polyaspartic and polyglutamic acids, polyolefin sulfonates, polyolefin phosphates, diphosphonates such as azacycloalkane-2,2-diphosphonates (e.g., azacycloheptane-2,2-diphosphonic acid), N-methyl azacyclopentane-2,3-diphosphonic acid, ethane-1-hydroxy-1,1-diphosphonic acid (EHDP) and ethane-1-amino-1,1-diphosphonate, phosphonoalkane carboxylic acids and salts of any of these agents, for example their alkali metal and ammonium salts.

Useful inorganic phosphate and polyphosphate salts illustratively include monobasic, dibasic and tribasic sodium phosphates, sodium tripolyphosphate (STPP), tetrapolyphosphate, mono-, di-, tri- and tetrasodium pyrophosphates, disodium dihydrogen pyrophosphate, sodium trimetaphosphate, sodium hexametaphosphate and the like, wherein sodium can optionally be replaced by potassium or ammonium. Other useful anticalculus agents include polycarboxylate polymers. These include polymers or copolymers of monomers that contain carboxylic acid groups, such as acrylic acid, methacrylic acid, and maleic acid or anhydride. Non-limiting examples include polyvinyl methyl ether/maleic anhydride (PVME/MA) copolymers, such as those available under the GANTREZ® brand from ISP, Wayne, N.J., United States of America. Still other useful anticalculus agents include sequestering agents including hydroxycarboxylic acids such as citric, fumaric, malic, glutaric and oxalic acids and salts thereof, and aminopolycarboxylic acids such as ethylenediaminetetraacetic acid (EDTA). One or more anticalculus agents are optionally present in the composition in an anticalculus effective total amount, such as about 0.01% to about 50%, for example about 0.05% to about 25% or about 0.1% to about 15% by weight.

In various embodiments, the anticalculus system comprises a mixture of sodium tripolyphsophate (STPP) and a tetrasodium pyrophosphate (TSPP). In various embodiments, the ratio of TSPP to STPP ranges from about 1:2 to about 1:4. In a preferred embodiment, the first anticalculus active ingredient, TSPP is present at about 1 to about 2.5% and the second anticalculus active ingredient, STPP is present at about 1 to about 10%.

In various embodiments, the anticalculus system further comprises a synthetic anionic polycarboxylate polymer, present for example, in an amount of about 0.1% to about 5%. In another embodiment, the synthetic anionic polycarboxylate may be present in an amount of about 0.5% to about 1.5%, most preferably at about 1% of the oral care composition. In one embodiment, the anticalculus system can include a copolymer of maleic anhydride and methyl vinyl ether, such as for example, the GANTREZ® S-97 product discussed above.

In various embodiments, the ratio of TSPP to STPP to the synthetic anionic polycarboxylate ranges from about 5:10:1 to about 5:20:10 (or 1:4:2). In one embodiment, the anticalculus system of the oral care composition comprises TSPP, STPP, and a polycarboxylate such as a copolymer of maleic anhydride and methyl vinyl ether at a ratio of about 1:7:1. In a non-limiting embodiment, the anticalculus system consists essentially of TSPP present at about 0.5% to about 2.5%, STPP present at about 1% to about 10%, and a copolymer of maleic anhydride and methyl vinyl ether present at about 0.5% to about 1.5%.

In a still further embodiment a composition of the invention may contain a thickening agent, useful, for example, to impart a desired consistency and/or mouth feel to the composition. Any orally acceptable thickening agent can be used, including without limitation carbomers, carboxyvinyl polymers, carrageenans, particularly ι-carrageenan (iota-carrageenan), cellulosic polymers such as hydroxyethylcellulose, carboxymethylcellulose (CMC) and salts thereof, e.g., CMC sodium, natural gums such as karaya, xanthan, gum arabic and tragacanth, colloidal magnesium aluminum silicate, colloidal silica and the like. One or more thickening agents are optionally present in a total amount of about 0.01% to about 15%, for example about 0.1% to about 10% or about 0.2% to about 5% by weight of the composition.

In a still further embodiment a composition of the invention may include at least one viscosity modifier. Any orally acceptable viscosity modifier can be used, including without limitation mineral oil, petrolatum, clays and organo-modified clays, fumed silica and the like. One or more viscosity modifiers may be optionally present in a total amount of about 0.01% to about 10%, for example about 0.1% to about 5% by weight of the composition.

In another embodiment the composition may contain a source of fluoride ions. One or more such sources can be present. Suitable sources of fluoride ions include fluoride, monofluorophosphate and fluorosilicate salts, and amine fluorides, including olaflur (N'-octadecyltrimethylendiamine-N,N,N'-tris(2-ethanol)-dihydrofluoride). Any such salt that is orally acceptable can be used, including without limitation alkali metal salts, and ammonium, stannous and indium salts. One or more fluoride-releasing salts are optionally present in an amount providing a total of about 100 to about 20,000 ppm, about 200 to about 5,000 ppm, or about 500 to about 2,500 ppm, fluoride ions to the composition. Where sodium fluoride is the sole fluoride-releasing salt present, illustratively an amount of about 0.01% to about 5%, about 0.05% to about 1% or about 0.1% to about 0.5%, sodium fluoride by weight may be present in the composition.

Other components suitable for inclusion in the composition include, without limitation, flavorants, colorants, and other active ingredients such as antioxidants and anti-inflammation agents. The components are formulated into oral compositions according to known procedures.

The orally acceptable vehicle or carrier in a lozenge bead or tablet may be a non-cariogenic, solid water-soluble polyhydric alcohol (polyol) such as mannitol, xylitol, sorbitol, malitol, hydrogenated starch hydrozylate, hydrogenated glucose, hydrogenated disaccharides, hydrogenated polysaccharides, and the like in an amount of about 85% to about 95% of the total composition. Emulsifiers such as glycerin, and tableting lubricants, in minor amounts of about 0.1% to 5%, may be incorporated into the tablet, bead or lozenge formulation to facilitate the preparation of the tablet beads and lozenges. Suitable lubricants include vegetable oils such as coconut oil, magnesium stearate, aluminum stearate, talc, starch and CARBOWAX®. Suitable non-cariogenic gums include kappa carrageenan, carboxymethyl cellulose, hydroxyethyl cellulose and the like.

The lozenge, bead or tablet may optionally be coated with a coating material such as waxes, shellac, carboxymethyl cellulose, polyethylene/maleic anhydride copolymer or kappa-carrageenan to further increase the time it takes the tablet or lozenge to dissolve in the mouth. The uncoated tablet or lozenge may be formulated to be slow dissolving, providing a sustained release rate of active ingredients of about 3 to 5 minutes. Accordingly, the solid dose tablet, bead and lozenge compositions of this embodiment affords a relatively longer time period of contact of the teeth in the oral cavity with the antibacterial and anticalculus active ingredients of the present invention.

Gum base materials for use in a gum form of the composition are well known in the art and include natural or synthetic gum bases thereof. Representative natural gums or elastomers include chicle, natural rubber, jelutong, balata, guttapercha, lechi caspi, sorva, guttakay, crown gum, and perillo, or mixtures thereof. Representative synthetic gums or elastomers include butadiene-styrene copolymers, polyisobutylene and isobutylene-isoprene copolymers. The gum base is incorporated in the chewing gum product at a concentration of about 10% to about 40% and preferably about 20% to about 35%.

The invention has been described above with respect to various preferred embodiments. Further non-limiting description is provided in the following examples.

EXAMPLES

Example 1

The dipropyl and dibutyl analogs of magnolol are synthesized by Friedel-Crafts acylation of 2,2'-diphenol with propanoyl chloride and butanoyl chloride respectively, followed by Clemmensen reduction to yield 5,5'-propyl-2,2'-dihydroxy-1,1'-biphenyl and 5,5'-dibutyl-2,2'-dihydroxy-1,1'-biphenyl, respectively.

Example 2

$MIC_{50}$ values against a variety of bacteria are measured for the dipropyl and dibutyl derivatives and compared to those for triclosan. Results are given in Table I. Lower numeric values correspond to more effective antibacterial activity.

TABLE I

| Bacteria | $MIC_{50}$ for dipropyl derivative | $MIC_{50}$ for dibutyl derivative | $MIC_{50}$ for triclosan |
| --- | --- | --- | --- |
| S. aureus | >500 | 7.8 | 2 |
| S. gordonii | >500 | 31.3 | 7.8 |
| S. mutans | >500 | 3.9 | 7.8 |
| E. corrodens | 1 | 0.5 | <0.001 |
| P. gingivalis | 3.9 | 2 | 0.5 |
| A. actino. | >500 | >500 | 0.125 |
| P. intermedia | 2 | 2 | 1 |
| P. nigresc. | 7.8 | 3.9 | 3.9 |
| F. nucleatum | >500 | >500 | 1 |
| M. catarrhalis | 7.8 | 15.6 | <0.001 |
| B. cereus | >500 | 31.3 | 15.6 |
| B. subtilis | >500 | 7.8 | 2 |

As can be seen from Table I against a number of *staphylococcus, streptococcus,* and *bacillus* bacteria in the Table, $MIC_{50}$ of the compound of formula (I) is over an order of magnitude less than that of the dipropyl derivative, and comparable to that of triclosan.

We claim:

1. A dentifrice composition selected from the group consisting of a tooth paste, gel, powder, a mouthwash and a mouth rinse comprising an antibacterial effective amount of a compound represented by formula (I):

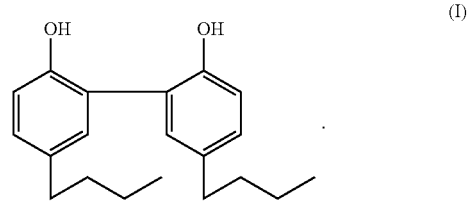

(I)

2. The composition of claim 1, wherein the compound represented by formula (I) is present in an amount of about 0.001% to about 10% by weight.

3. A tooth paste or gel composition comprising a humectant;

an abrasive compound; and an antibacterial effective amount of a compound represented by formula (I)

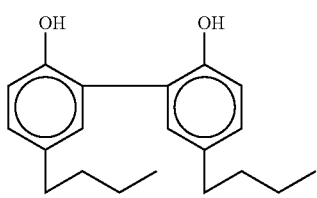

4. The composition of claim 3, further comprising an anticalculus agent.

5. The composition of claim 4, wherein the anticalculus agent comprises a phosphate compound.

6. The composition of claim 4, wherein the anticalculus agent comprises tetrasodium pyrophosphate and trisodium polyphosphate.

7. The composition of claim 4, wherein the anticalculus agent comprises a synthetic anionic polycarboxylate.

8. The composition of claim 3, further comprising a maleic anhydride copolymer with methyl vinyl ether.

9. The composition of claim 3, comprising tetrasodium pyrophosphate and trisodium polyphosphate in a weight ratio of about 1:7.

10. The composition of claim 1, further comprising an agent selected from triclosan, delmopinal, cetyl pyridinium chloride, a zinc iron source, a stannous ion source, an anti-inflammatory agent and botanical agents.

11. A method for inhibiting bacterial growth in the oral cavity comprising applying to the surfaces of the oral cavity a composition comprising a compound represented by formula (I):

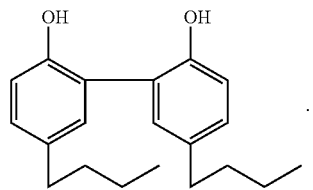

12. The method of claim 10, wherein applying comprises brushing the teeth.

13. The method of claim 10, wherein the composition further comprises a maleic anhydride copolymer with methyl vinyl ether.

14. The method of claim 10, wherein the composition further comprises an agent selected from an anticalculus agent, a phosphate compound, tetrasodium pyrophosphate and trisodium polyphosphate.

15. The method of claim 11, further comprising an agent selected from triclosan, delmopinal, cetyl pyridinium chloride, a zinc iron source, a stannous ion source, an anti-inflammatory agent and botanical agents.

16. A method of treating gingivitis, periodontal disease, and/or ameliorating oral malodor comprising topically administering a dentifrice composition to the surface of the oral cavity, the dentifrice composition comprising an antibacterial effective amount of a compound represented by formula (I):

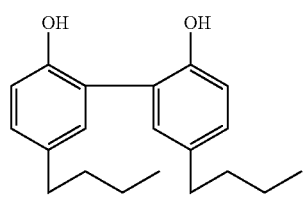

17. The method of claim 16, wherein the compound represented by formula (I) is present in the composition in an amount of about 0.001% to about 10% by weight.

18. The method of claim 16, wherein he composition further comprises an agent selected from triclosan, delmopinal, cetyl pyridinium chloride, a zinc iron source, a stannous ion source, an anti-inflammatory agent and botanical agents.

* * * * *